United States Patent
Nielsen et al.

(10) Patent No.: US 10,174,043 B1
(45) Date of Patent: Jan. 8, 2019

(54) SYNTHESIS OF A 1,2,5,6-NAPHTHALENEDIIMIDE MONOMER

(71) Applicant: PHILLIPS 66 COMPANY, Houston, TX (US)

(72) Inventors: Laura Nielsen, Bartlesville, OK (US); Kathy Woody, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 16/038,291

(22) Filed: Jul. 18, 2018

Related U.S. Application Data

(60) Provisional application No. 62/538,386, filed on Jul. 28, 2017.

(51) Int. Cl.
*C07D 487/22* (2006.01)

(52) U.S. Cl.
CPC .................. *C07D 487/22* (2013.01)

(58) Field of Classification Search
CPC .................................... C07D 487/22
USPC ....................................... 548/423
See application file for complete search history.

(56) References Cited

U.S. PATENT DOCUMENTS 9,502,473 B2   11/2016   Lee et al.

OTHER PUBLICATIONS

Shan-ci Chen, Qikai Zhang, Qingdong Zheng, Changquan Tang and Can Zhong Lu, "Angular-Shaped Naphthalene Tetracarboxylic Diimides for N-Channel Organic Transistor Semiconductors", ChemComm Communication, 2012, vol. 48, pp. 1254-1256.

Zheng Zhao, Fengjiao Zhang, Xu Zhyang, Xiaodi Yang, Hongxiang Li, Xike Gao, Chong-an Di, and Daoben Zhu, '1,2,5,6-Naphthalenediimide Based Donor-Acceptor Copolymers Designed from Isomer Chemistry for Organic Semiconducting Materials, Macromolecules Article, 2013, vol. 46, pp. 7705-7714.

*Primary Examiner* — Kristin A Vajda
(74) *Attorney, Agent, or Firm* — Phillips 66 Company

(57) ABSTRACT

A method comprising converting 2,6-naphthalene diol to produce

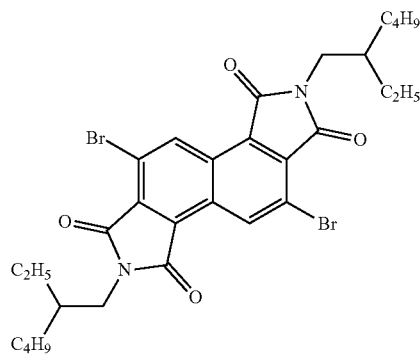

wherein the method occurs at temperatures less than 250° C.

12 Claims, 8 Drawing Sheets

SYNTHESIS OF A 1,2,5,6-NAPHTHALENEDIIMIDE MONOMER

CROSS-REFERENCE TO RELATED APPLICATIONS

This application is a non-provisional application which claims the benefit of and priority to U.S. Provisional Application Ser. No. 62/538,386 filed Jul. 28, 2017, entitled "Synthesis of a 1,2,5,6-Naphthalenediimide Monomer", which is hereby incorporated by reference in its entirety.

STATEMENT REGARDING FEDERALLY SPONSORED RESEARCH OR DEVELOPMENT

None.

FIELD OF THE INVENTION

This invention relates to high performance wide-bandgap polymers for organic photovoltaics.

BACKGROUND OF THE INVENTION

Solar energy using photovoltaics requires active semiconducting materials to convert light into electricity. Currently, solar cells based on silicon are the dominating technology due to their high-power conversion efficiency. Recently, solar cells based on organic materials showed interesting features, especially on the potential of low cost in materials and processing.

Organic photovoltaic cells have many potential advantages when compared to traditional silicon-based devices. Organic photovoltaic cells are light weight, economical in the materials used, and can be deposited on low cost substrates, such as flexible plastic foils. However, organic photovoltaic devices typically have relatively low power conversion efficiency (the ratio of incident photons to energy generated). This is, in part, thought to be due to the morphology of the active layer. The charge carriers generated must migrate to their respective electrodes before recombination or quenching occurs. The diffusion length of an exciton is typically much less than the optical absorption length, requiring a tradeoff between using a thick, and therefore resistive, cell with multiple or highly folded interfaces, or a thin cell with a low optical absorption efficiency.

Angular-shaped 1,2,5,6-naphthalene tetracarboxylic diimide (NDI) monomers have demonstrated high conductivity in other organic electronic applications. However traditional synthetic routes created safety concerns due to the use of a toxic cyanide reagent and the use of a stainless steel autoclave for a high temperature oxidation reaction. Please see FIG. 1 for a traditional partial synthesis of NDI. There exists a need to find a synthesis method to produce NDI monomers safely.

BRIEF SUMMARY OF THE DISCLOSURE

A method comprising converting 2,6-naphthalene diol to produce

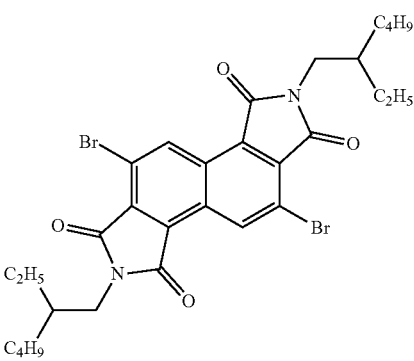

wherein the method occurs at temperatures less than 250° C.

An alternate method comprising:

brominating 2,6-naphthalene diol to produce:

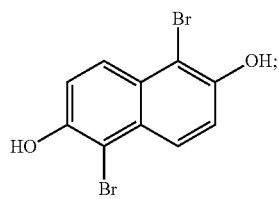

converting the diols of

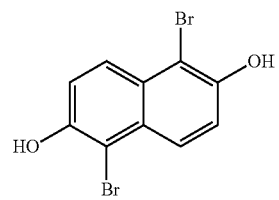 [SMILES: Oc1ccc2c(Br)c(O)ccc2c1Br]

to produce

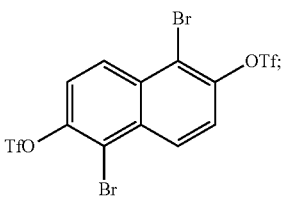 [SMILES: O=S(=O)(Oc1ccc2c(Br)c(OS(=O)(=O)C(F)(F)F)ccc2c1Br)C(F)(F)F]

Sonogashira coupling

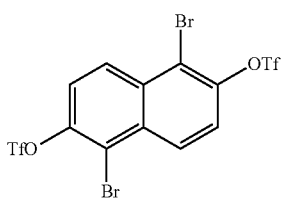 [SMILES: O=S(=O)(Oc1ccc2c(Br)c(OS(=O)(=O)C(F)(F)F)ccc2c1Br)C(F)(F)F]

to produce:

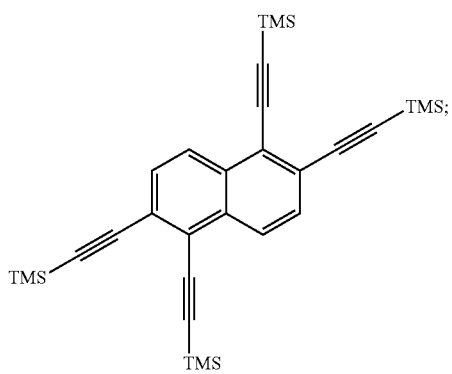 [SMILES: C[Si](C)(C)C#Cc1ccc2c(C#C[Si](C)(C)C)c(C#C[Si](C)(C)C)ccc2c1C#C[Si](C)(C)C]

oxidizing

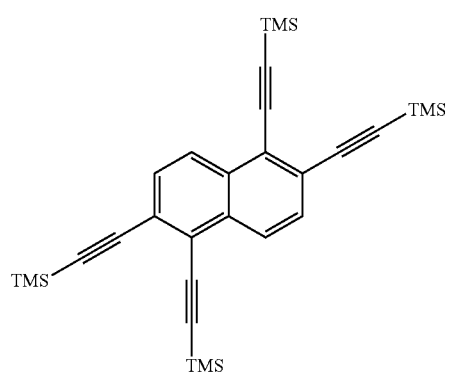 [SMILES: C[Si](C)(C)C#Cc1ccc2c(C#C[Si](C)(C)C)c(C#C[Si](C)(C)C)ccc2c1C#C[Si](C)(C)C]

to produce:

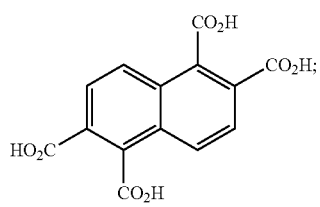

cyclizing

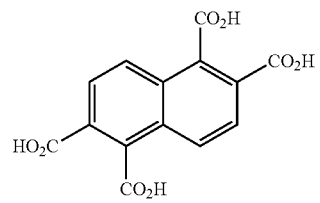 [SMILES: O=C(O)c1ccc2c(C(=O)O)c(C(=O)O)ccc2c1C(=O)O]

to produce:

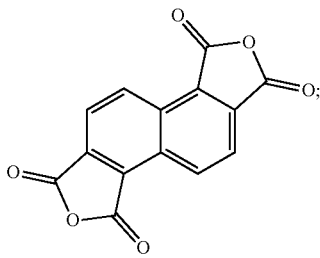 [SMILES: O=c1oc(=O)c2c1ccc1c2ccc2c(=O)oc(=O)c21]

converting

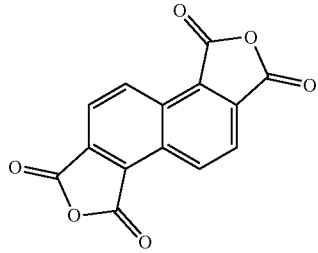 [SMILES: O=c1oc(=O)c2c1ccc1c2ccc2c(=O)oc(=O)c21]

to produce:

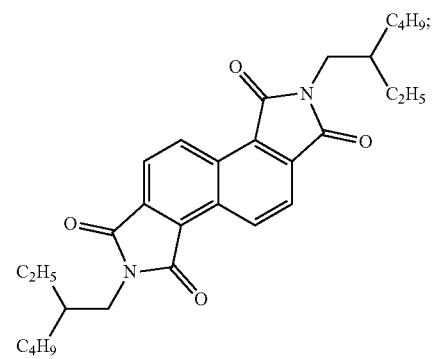

brominating

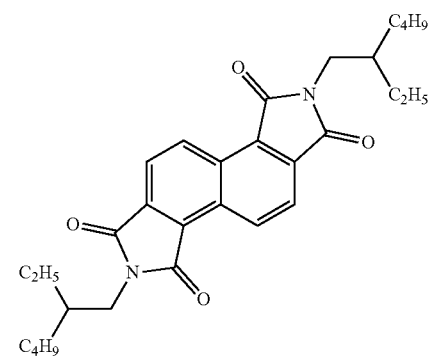

to produce:

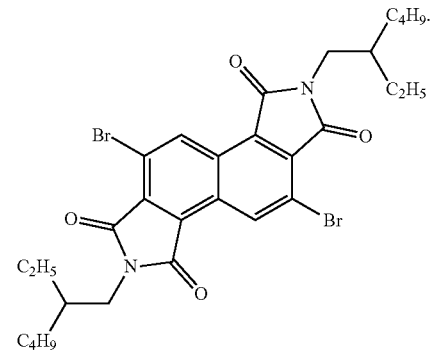

Yet another method comprising:
reacting 2,6-naphthalene diol in tetrahydofuran with N-bromosuccinimide, at a temperature below about 20° C., to produce reaction mixture A, reaction mixture A is then diluted with $Na_2S_2O_3$, at a temperature greater than about 20° C. and less than 250° C., and filtered to produce

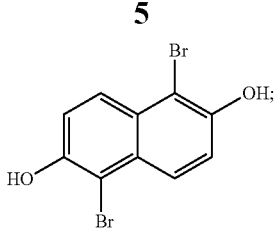

reacting

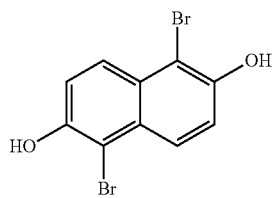 [SMILES: Oc1ccc2c(Br)c(O)ccc2c1Br]

with triflic anhydride, at a temperature below about 20° C., followed by pyridine, at a temperature below about 20° C., to produce reaction mixture B, reaction mixture B is then diluted with dichloromethane and fractionated to produce

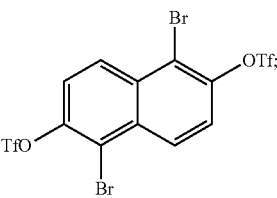 [SMILES: O=S(=O)(Oc1ccc2c(Br)c(OS(=O)(=O)C(F)(F)F)ccc2c1Br)C(F)(F)F]

reacting

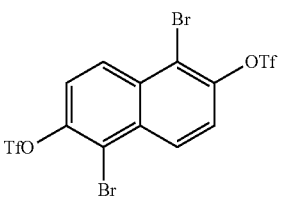 [SMILES: O=S(=O)(Oc1ccc2c(Br)c(OS(=O)(=O)C(F)(F)F)ccc2c1Br)C(F)(F)F]

with CuI and Pd(PPh$_3$)$_2$Cl$_2$, followed by trimethylamine and trimethylsilylacetylene to produce reaction mixture C, reaction mixture C is then extracted with dicholoromethane and fractionated to produce

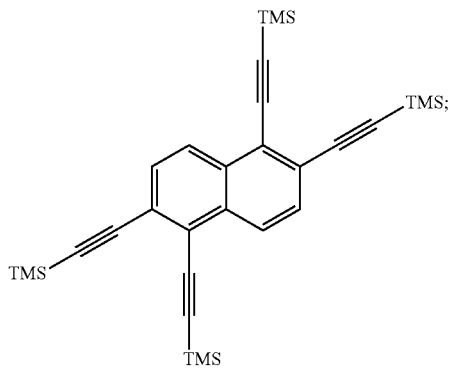 [SMILES: C[Si](C)(C)C#Cc1ccc2c(C#C[Si](C)(C)C)c(C#C[Si](C)(C)C)ccc2c1C#C[Si](C)(C)C]

reacting

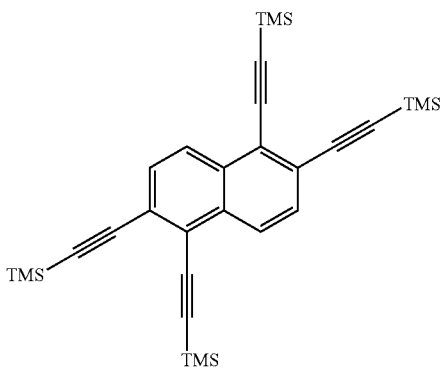 [SMILES: C[Si](C)(C)C#Cc1ccc2c(C#C[Si](C)(C)C)c(C#C[Si](C)(C)C)ccc2c1C#C[Si](C)(C)C]

with FeCl$_3$ and a tert-butylhydroperoxide solution followed by a NaOH treatment and acidification with HCl to produce reaction mixture D, reaction mixture D is then filtered and dried to produce

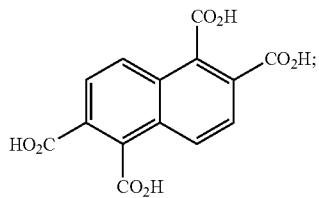 [SMILES: O=C(O)c1ccc2c(C(=O)O)c(C(=O)O)ccc2c1C(=O)O]

reacting

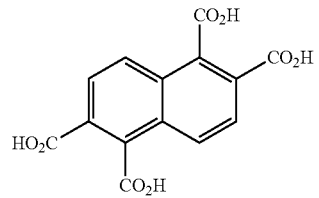

with acetic anhydride, at temperature greater than about 20° C. and less than 250° C., to produce reaction mixture E which comprises:

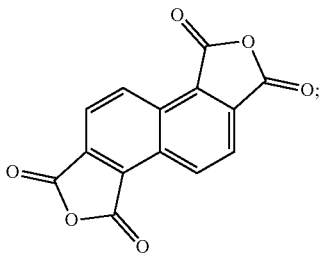 [SMILES: O=c1oc(=O)c2c1ccc1c2ccc2c(=O)oc(=O)c21]

reacting

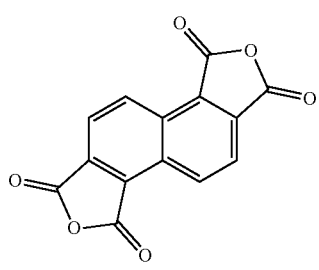 [SMILES: O=c1oc(=O)c2c1ccc1c2ccc2c(=O)oc(=O)c21]

with 2-ethylhexylamine and toluene, at temperature greater than about 20° C. and less than 250° C., followed by reacting with thionyl chloride to produce reaction mixture F, reaction mixture F is then purified to produce

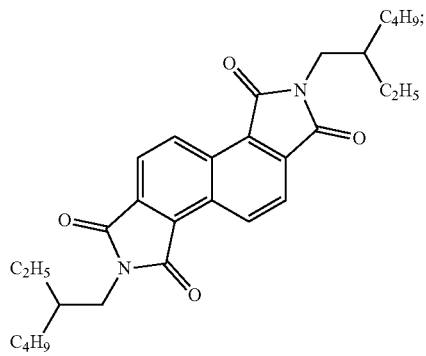

reacting

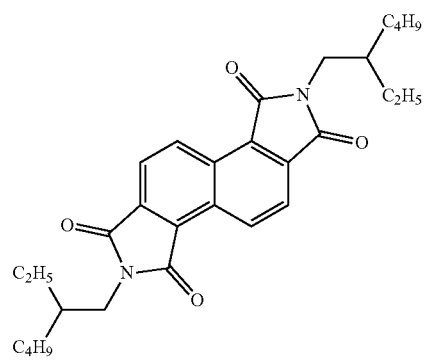

with N-bromosuccinimide, at temperature greater than about 20° C. and less than 250° C., to produce reaction mixture G, reaction mixture G is then purified to produce

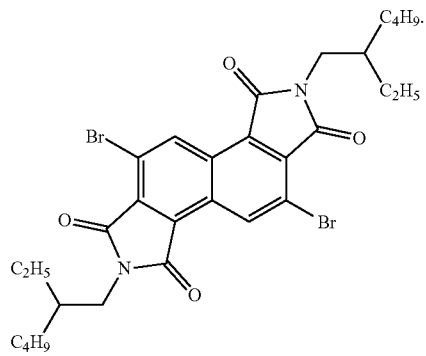

BRIEF DESCRIPTION OF THE DRAWINGS

A more complete understanding of the present invention and benefits thereof may be acquired by referring to the follow description taken in conjunction with the accompanying drawings in which:

FIG. 2 depicts the 1H NMR spectrum of

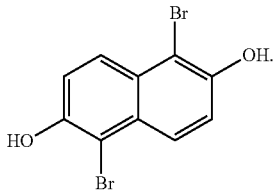 [SMILES: Oc1ccc2c(Br)c(O)ccc2c1Br]

Figure 3:
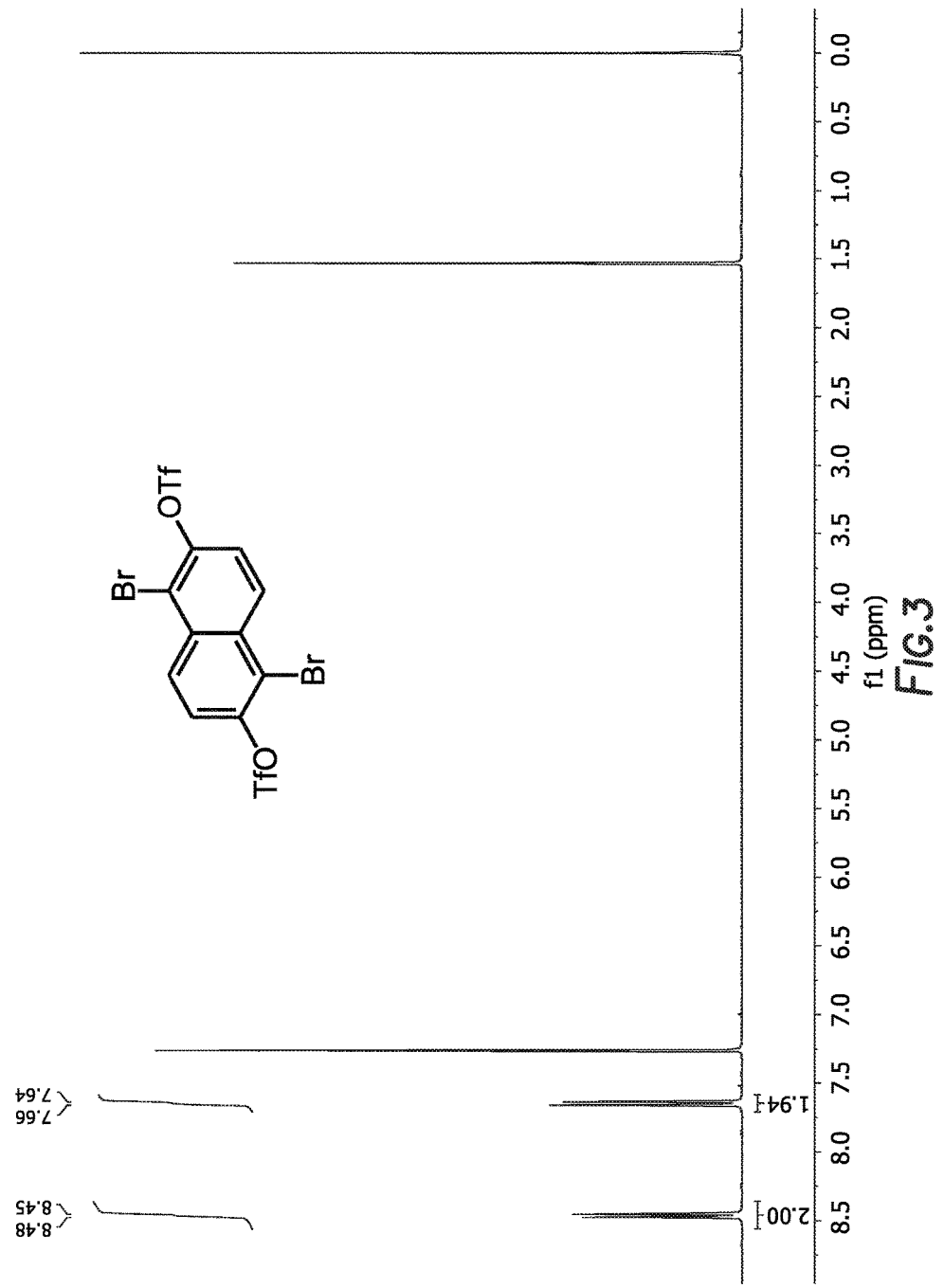

FIG. 3 depicts the 1H NMR spectrum of

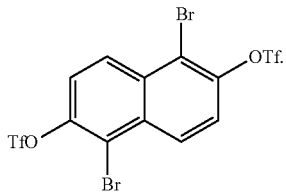 [SMILES: O=S(=O)(Oc1ccc2c(Br)c(OS(=O)(=O)C(F)(F)F)ccc2c1Br)C(F)(F)F]

Figure 4:
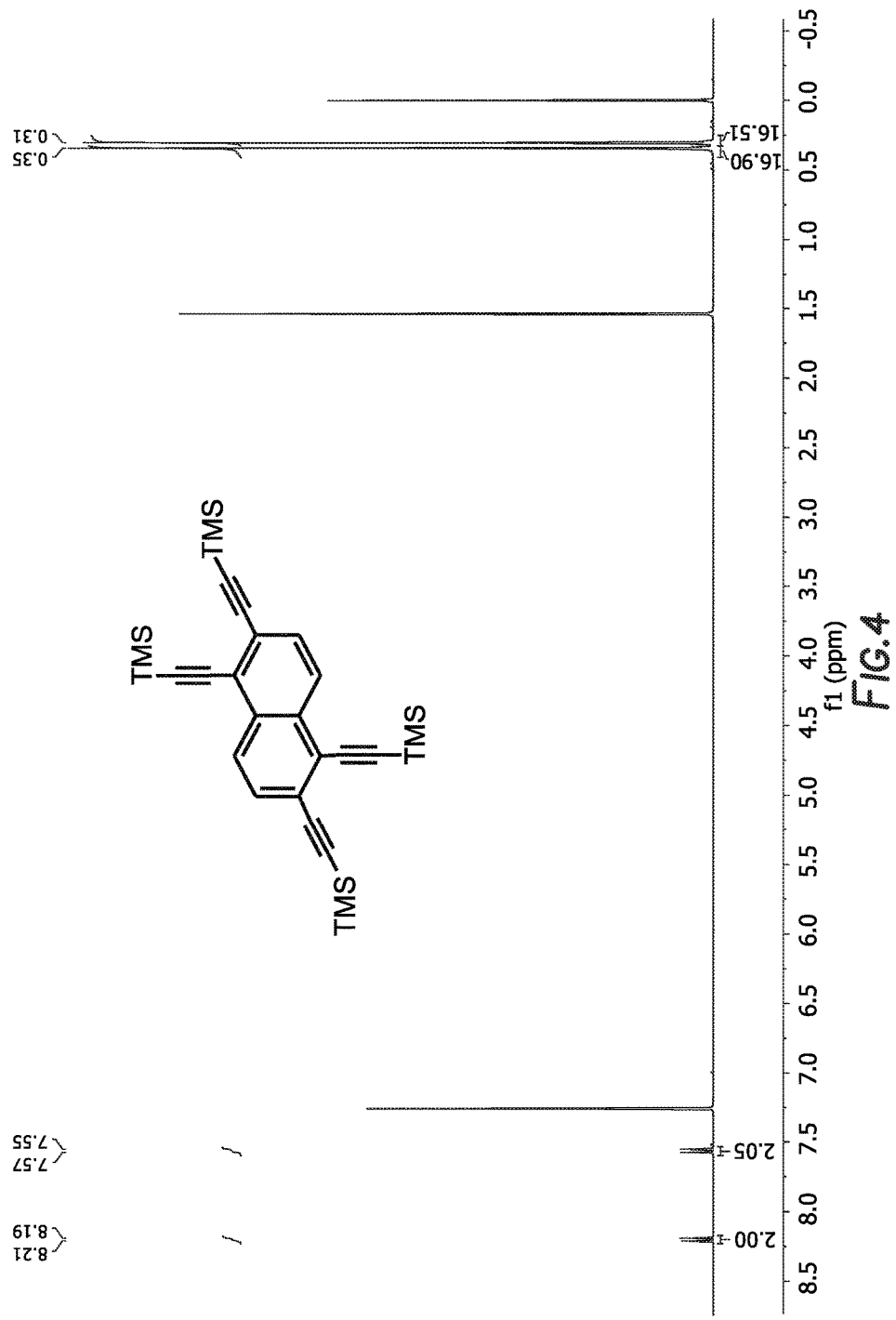

FIG. 4 depicts the 1H NMR spectrum of

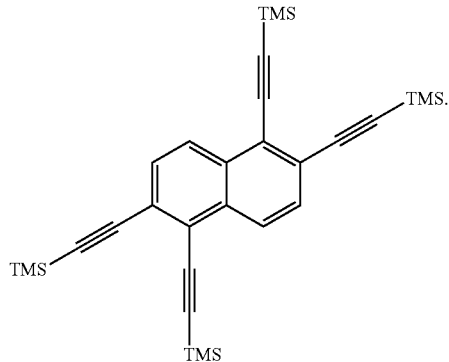 [SMILES: C[Si](C)(C)C#Cc1ccc2c(C#C[Si](C)(C)C)c(C#C[Si](C)(C)C)ccc2c1C#C[Si](C)(C)C]

Figure 5:
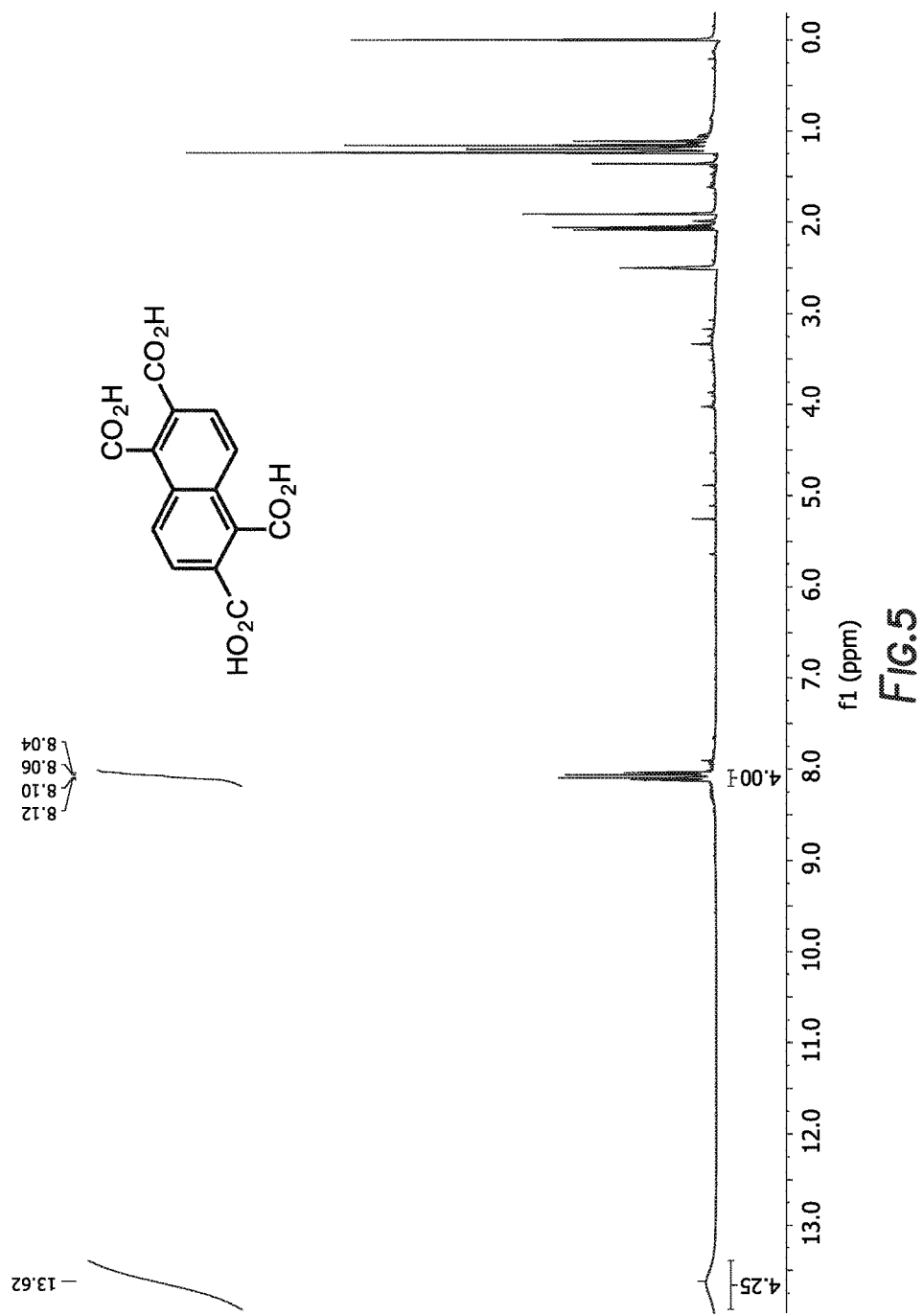

FIG. 5 depicts the 1H NMR spectrum of

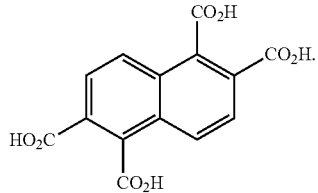

Figure 6:
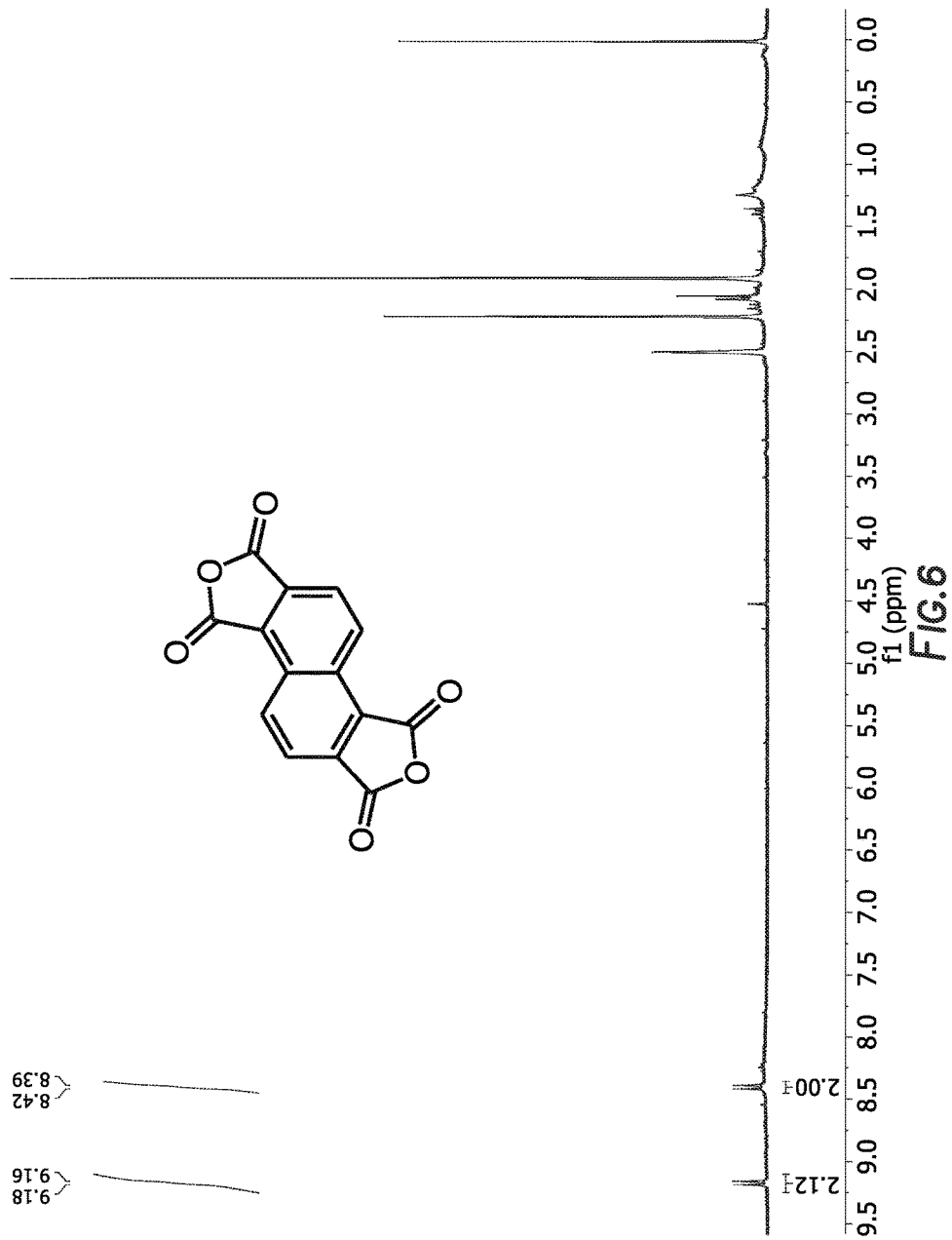

FIG. 6 depicts the 1H NMR spectrum of

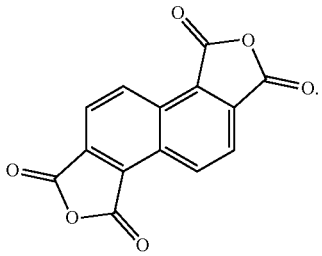 [SMILES: O=c1oc(=O)c2c1ccc1c2ccc2c(=O)oc(=O)c21]

Figure 7:
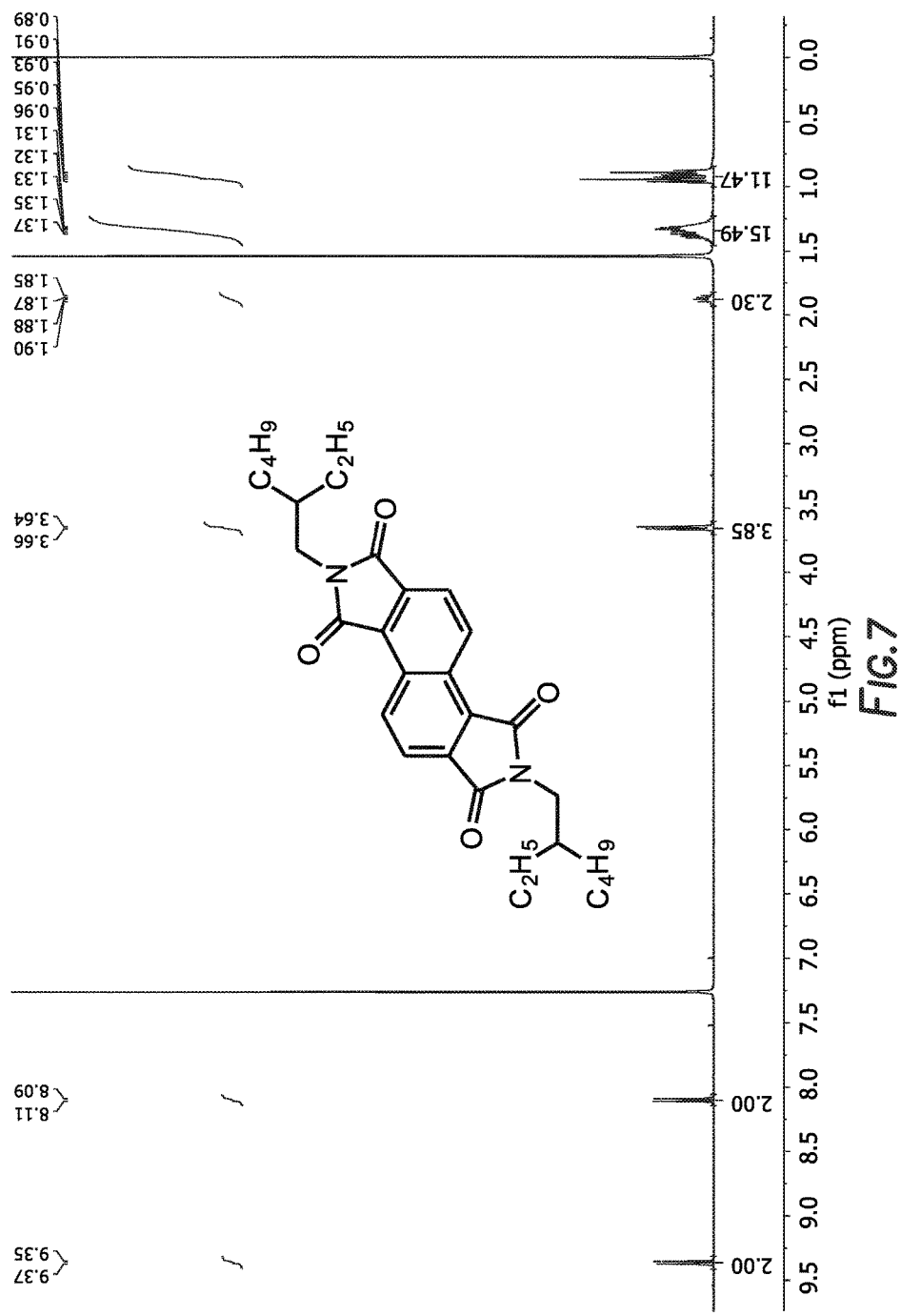

FIG. 7 depicts the 1H NMR spectrum of

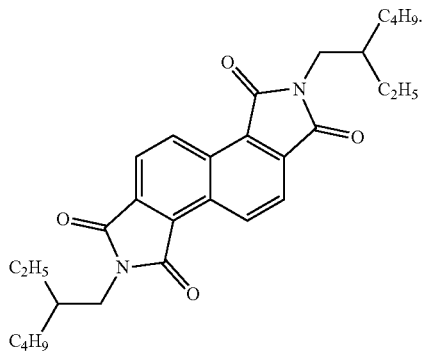

Figure 8:
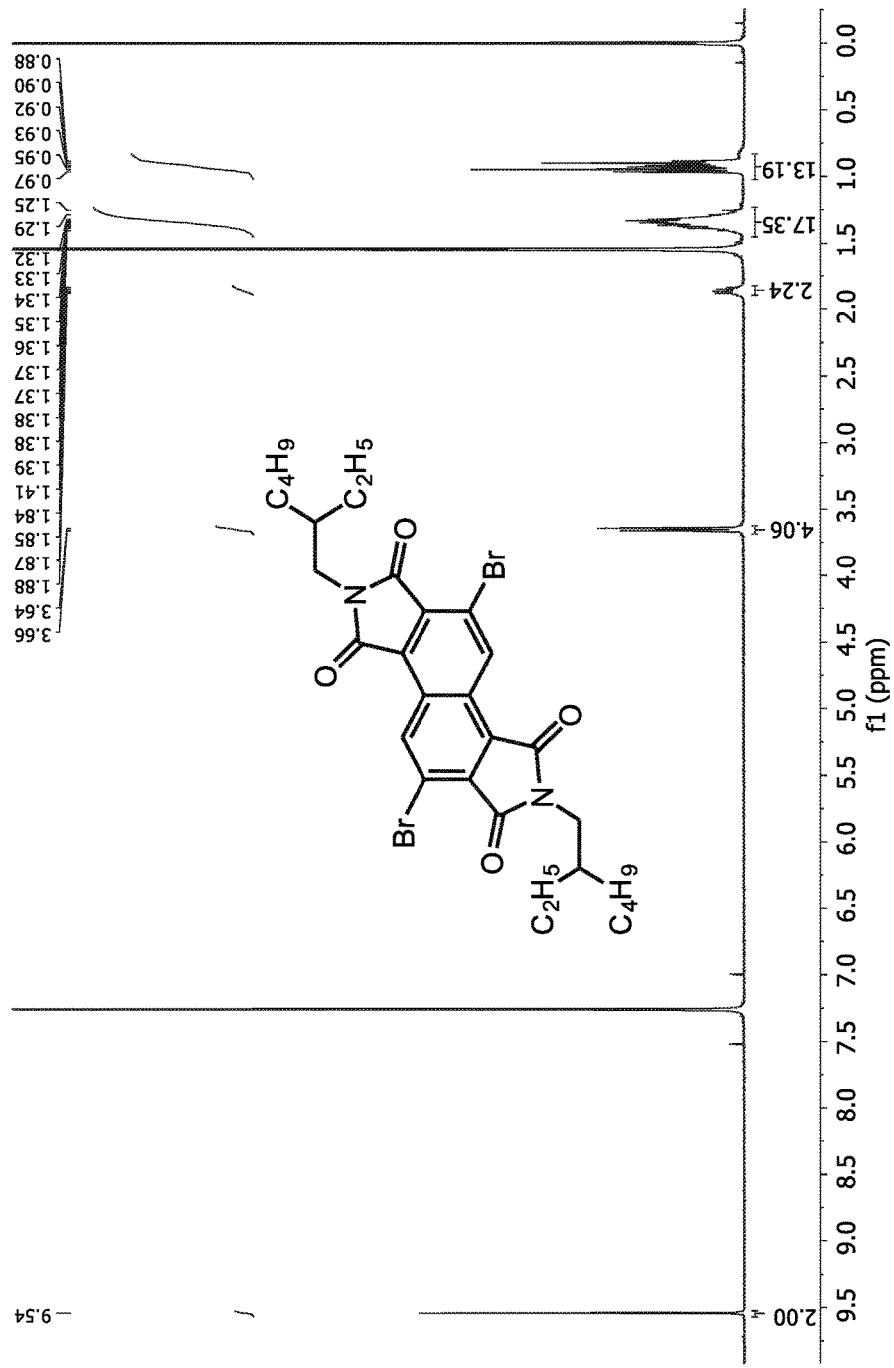

FIG. 8 depicts the 1H NMR spectrum of

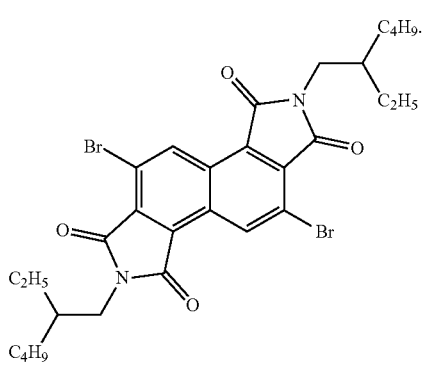

DETAILED DESCRIPTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

The following examples of certain embodiments of the invention are given. Each example is provided by way of explanation of the invention, one of many embodiments of the invention, and the following examples should not be read to limit, or define, the scope of the invention.

Method of Synthesizing a 1,2,5,6-Naphthalenediimide Monomer

The method involves converting 2,6-naphthalene diol to produce

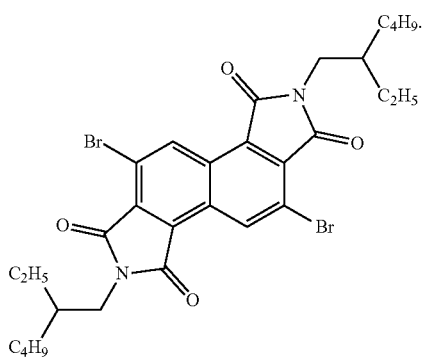

In one embodiment of the method, the temperature does not exceed about 290° C. In other embodiments, none of the reactions in this method exceed 280° C., 270° C., 260° C., 250° C., 240° C., 230° C., 220° C., 210° C., 200° C., 190° C., 180° C., 170° C., 160° C., or even 150° C. In yet another embodiment, the conversion from 2,6-naphthalene diol to produce

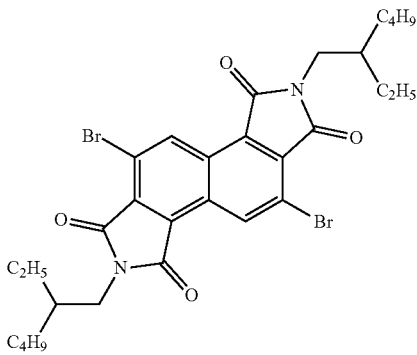

does not contain cyanide-containing reagents.

In one embodiment, the method begins by brominating 2,6-naphthalene diol to produce:

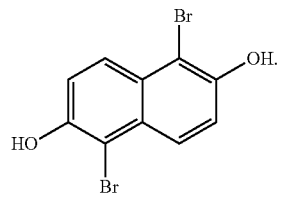 [SMILES: Oc1ccc2c(Br)c(O)ccc2c1Br]

The diols of

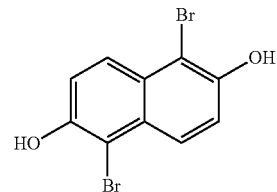 [SMILES: Oc1ccc2c(Br)c(O)ccc2c1Br]

are then converted into

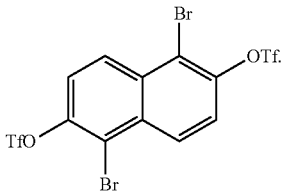 [SMILES: O=S(=O)(Oc1ccc2c(Br)c(OS(=O)(=O)C(F)(F)F)ccc2c1Br)C(F)(F)F]

During this conversion the triflic anhydride can either be added before the pyridine or after the pyridine.

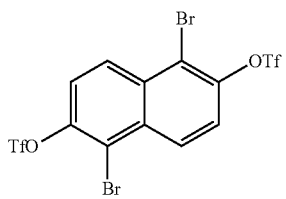 [SMILES: O=S(=O)(Oc1ccc2c(Br)c(OS(=O)(=O)C(F)(F)F)ccc2c1Br)C(F)(F)F]

is then exposed to a Sonogashira coupling condition to form

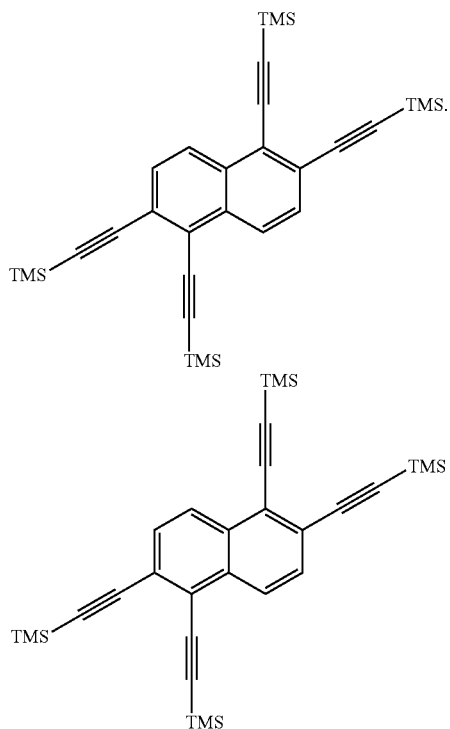

was then oxidized to produce:

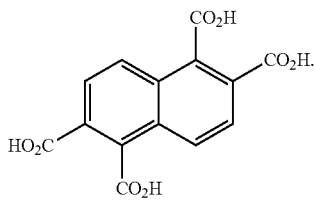 [SMILES: O=C(O)c1ccc2c(C(=O)O)c(C(=O)O)ccc2c1C(=O)O]

This was then followed by cyclizing

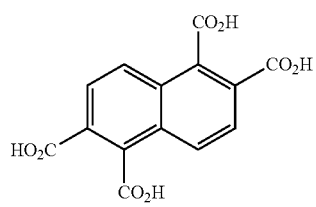

to produce

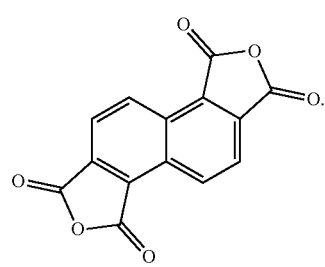 [SMILES: O=c1oc(=O)c2c1ccc1c2ccc2c(=O)oc(=O)c21]

A conversion of

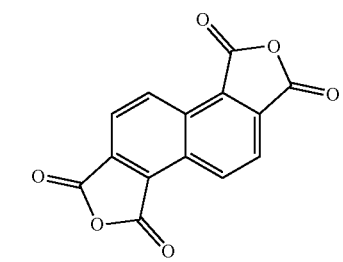 [SMILES: O=c1oc(=O)c2c1ccc1c2ccc2c(=O)oc(=O)c21]

to produce

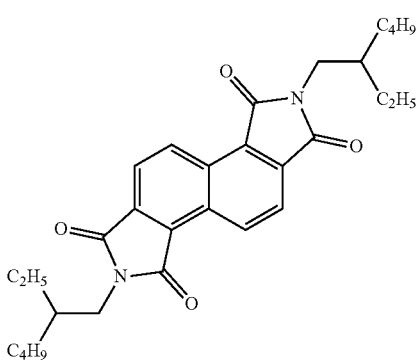

followed by a bromination to produce

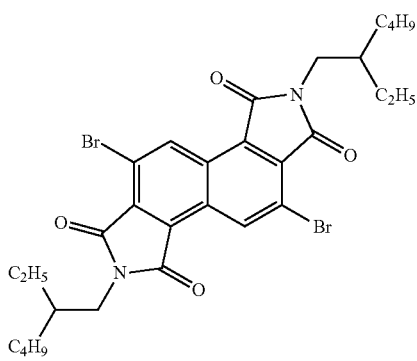

completes the method.

In one embodiment the method can also be expressed as a series of reactions. In this method reacting 2,6-naphthalene diol to produce reaction mixture A, wherein reaction mixture A comprises:

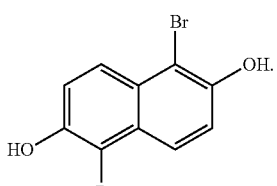

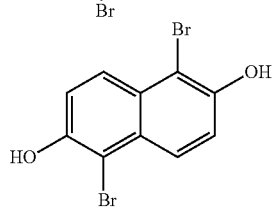

is then reacted to produce reaction mixture B, wherein reaction mixture B comprises:

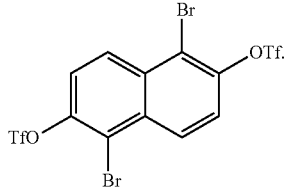 [SMILES: O=S(=O)(Oc1ccc2c(Br)c(OS(=O)(=O)C(F)(F)F)ccc2c1Br)C(F)(F)F]

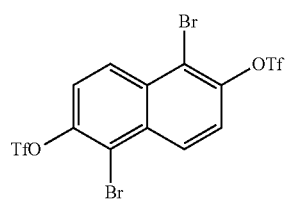 [SMILES: O=S(=O)(Oc1ccc2c(Br)c(OS(=O)(=O)C(F)(F)F)ccc2c1Br)C(F)(F)F]

is then reacted to produce reaction mixture C, wherein reaction mixture C comprises:

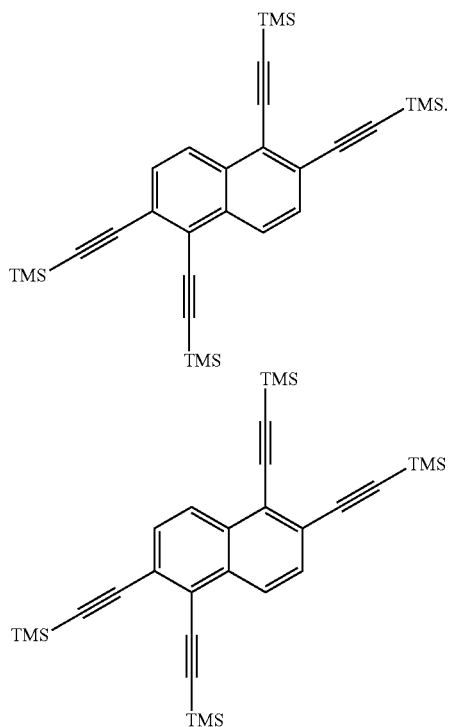

is then reacted to produce reaction mixture D, wherein reaction mixture D comprises

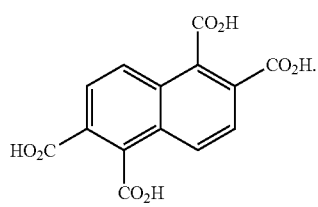

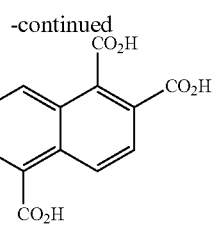

is then reacted to produce reaction mixture E, wherein reaction mixture E comprises:

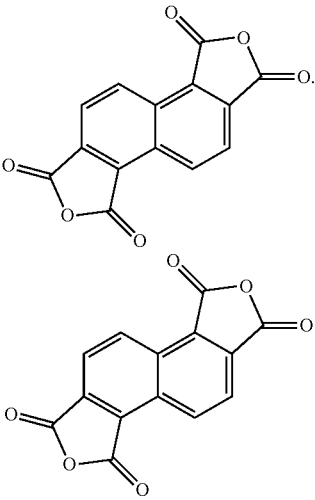

is then reacted to produce reaction mixture F, wherein reaction mixture F comprises:

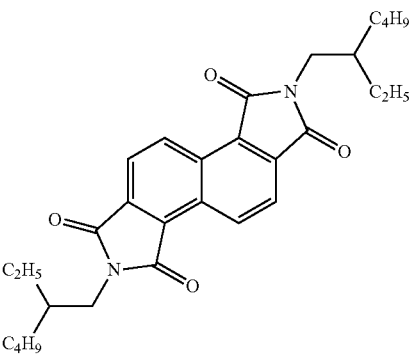

The final reaction involves reacting

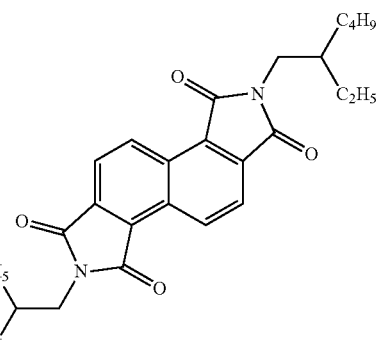

to produce reaction mixture G, wherein reaction mixture G comprises:

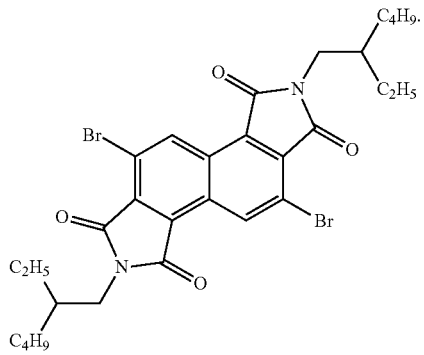

In a more detailed embodiment, the method begins by taking a solution of 2,6-naphthalene diol (10.16 g, 63.43 mmol) in tetrahydrofuran (110 mL) and cooling the solution to about 0° C., then treated slowly with N-bromosuccinimide (22.58 g, 0.13 mol). The flask was then topped with a water condenser and heated to around 60° C. for around 3 hours, then cooled to room temperature. This reaction mixture A was diluted with a saturated aqueous $Na_2S_2O_3$ solution (~250 mL) and water (~1.5 L), and the resulting solid was collected by filtration, and then left under vacuum for around 18 hours. The desired product,

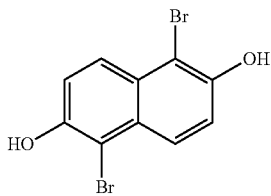 [SMILES: Oc1ccc2c(Br)c(O)ccc2c1Br]

(19.5 g, 0.061 mol, 97% yield), was obtained as a tan solid. The 1H NMR spectrum of

Figure 1:
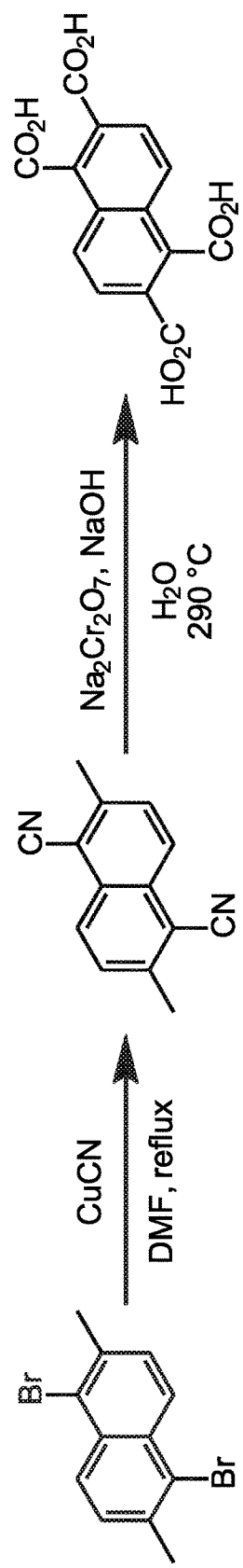
FIG. 1 depicts the traditional partial synthesis of NDI.
Figure 2:
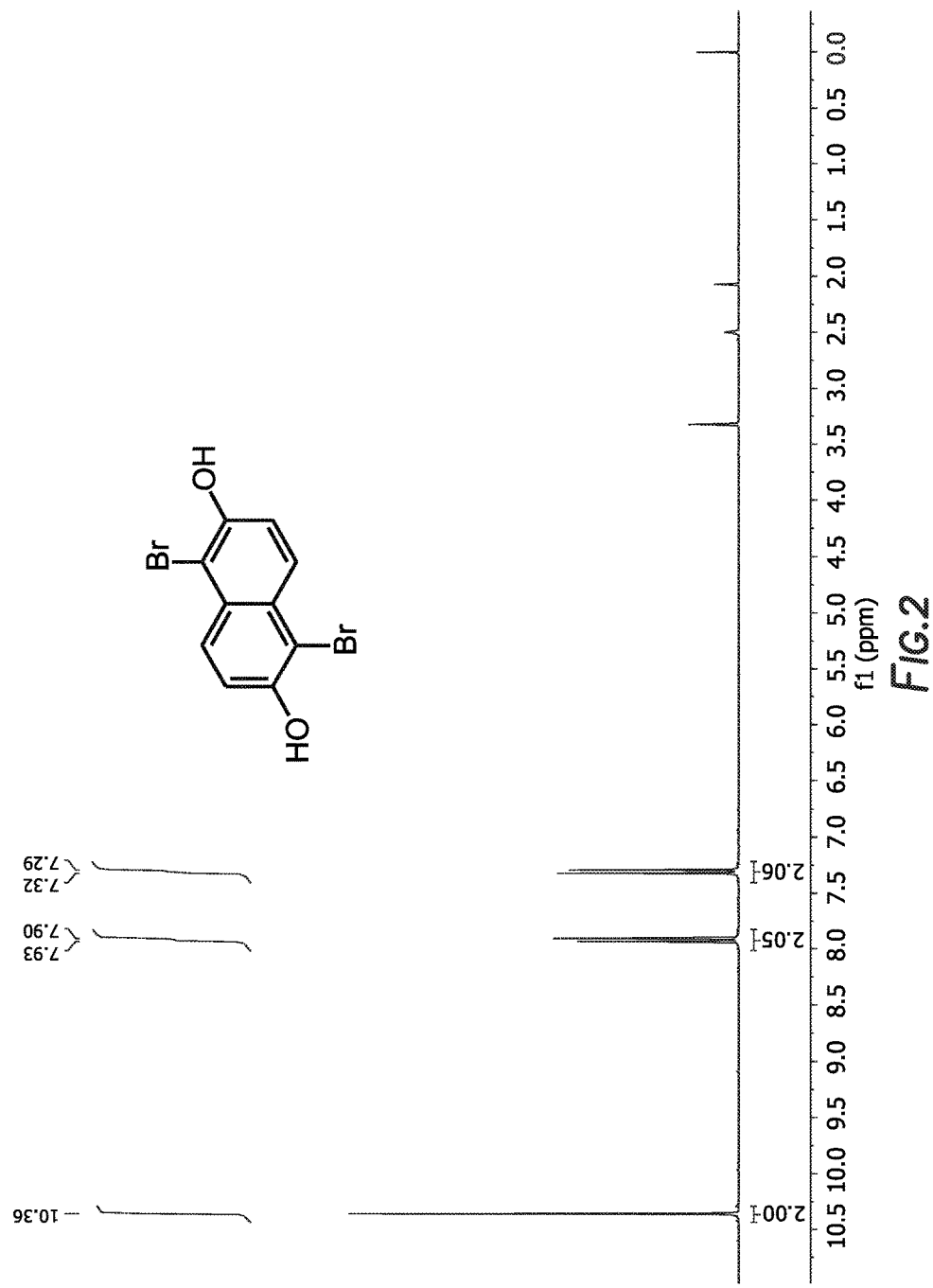

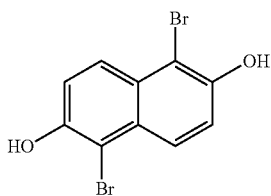 [SMILES: Oc1ccc2c(Br)c(O)ccc2c1Br]

is shown in FIG. 2.

The next reaction in the method involves charging

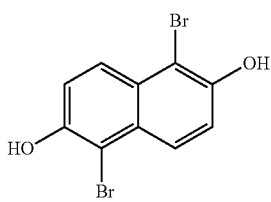 [SMILES: Oc1ccc2c(Br)c(O)ccc2c1Br]

in a Schlenk flask. A hot, oven-dried Schlenk flask was evacuated for about 30 min, refilled with argon, then charged with

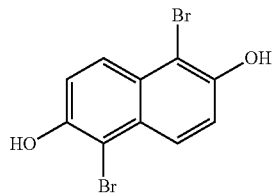 [SMILES: Oc1ccc2c(Br)c(O)ccc2c1Br]

(10 g, 31.45 mmol) and evacuated for about 1 hour. The flask was refilled with argon and dry dichloromethane (300 mL) was added. The resulting suspension was cooled to about 0° C. for about 15 min, then triflic anhydride (11.62 mL, 0.069 mol) was added dropwise, followed by the dropwise addition of pyridine (15.2 mL, 0.189 mol). The reaction was then gradually warmed to room temperature and stirred for about 18 hours. The reaction mixture was diluted with dichloromethane and water, then transferred to a separatory funnel. The aqueous layer was acidified with hydrochloric acid, then extracted with dichloromethane. The combined organic extracts were dried ($MgSO_4$), filtered, and concentrated into reaction mixture B. Reaction mixture B was then diluted with a mixture of dichloromethane and acetone, applied to the top of a 4"×6" column, and eluted with dichloromethane. All fractions containing

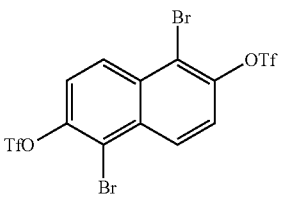 [SMILES: O=S(=O)(Oc1ccc2c(Br)c(OS(=O)(=O)C(F)(F)F)ccc2c1Br)C(F)(F)F]

were concentrated. The material was then dissolved in dichloromethane, adsorbed onto silica gel and purified on a 340 g Biotage silica gel cartridge with a 10-30% dichloromethane/hexanes gradient. Fractions containing pure product

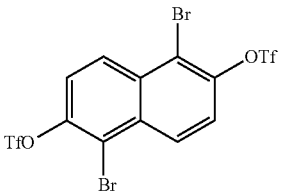 [SMILES: O=S(=O)(Oc1ccc2c(Br)c(OS(=O)(=O)C(F)(F)F)ccc2c1Br)C(F)(F)F]

were concentrated (15.2 g, 0.026 mol, 83% yield) and was a white, crystalline solid. The 1H NMR spectrum of

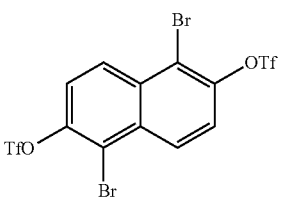 [SMILES: O=S(=O)(Oc1ccc2c(Br)c(OS(=O)(=O)C(F)(F)F)ccc2c1Br)C(F)(F)F]

is shown in FIG. 3.

The next reaction in the method involves first taking a hot, oven-dried Schlenk flask and evacuating for about 1 hour, followed by refilled with argon.

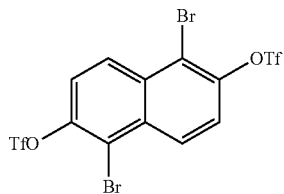 [SMILES: O=S(=O)(Oc1ccc2c(Br)c(OS(=O)(=O)C(F)(F)F)ccc2c1Br)C(F)(F)F]

(11.6 g, 19.9 mmol), CuI (1.14 g, 6 mmol), and Pd(PPh$_3$)$_2$Cl$_2$ (2.1 g, 3 mmol) are then added to the flask, and then degassed for about 30 min. After refilling with argon, dry tetrahydrofuran (50 mL, mol) was added, and two freeze-pump-thaw cycles were performed. The mixture was then warmed to room temperature and treated with triethylamine (16.7 mL, 120 mmol) and trimethylsilylacetylene (28.4 mL, 200 mmol). The reaction was then stirred at about 40° C. for about 3 days. The reaction mixture C was cooled to room temperature, then poured into water and extracted with dichloromethane. The combined organic extracts were dried (MgSO4), filtered, and concentrated. The crude material was dissolved in dichloromethane, adsorbed onto silica gel and purified on a 340 g Biotage column with a 0-15% dichloromethane/hexanes gradient. Any fractions containing product were concentrated to produce

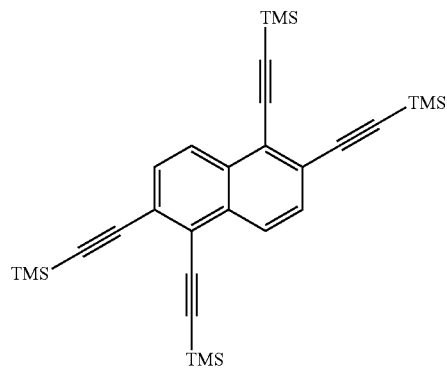 [SMILES: C[Si](C)(C)C#Cc1ccc2c(C#C[Si](C)(C)C)c(C#C[Si](C)(C)C)ccc2c1C#C[Si](C)(C)C]

(8.3 g, 16 mmol, 62% yield) as an orange solid. The 1H NMR spectrum of

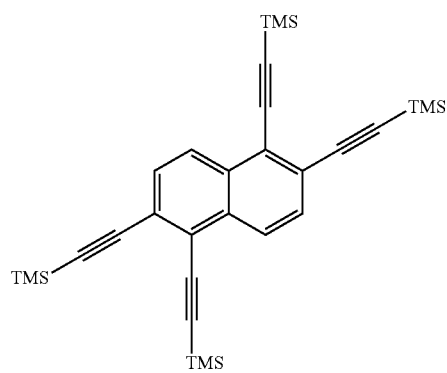 [SMILES: C[Si](C)(C)C#Cc1ccc2c(C#C[Si](C)(C)C)c(C#C[Si](C)(C)C)ccc2c1C#C[Si](C)(C)C]

is shown in FIG. 4.

In a flask,

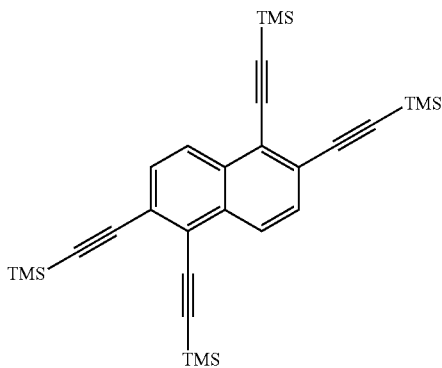 [SMILES: C[Si](C)(C)C#Cc1ccc2c(C#C[Si](C)(C)C)c(C#C[Si](C)(C)C)ccc2c1C#C[Si](C)(C)C]

(3.78 g, 7.4 mmol), FeCl$_3$(H$_2$O)$_6$ (0.4 g, 1.5 mmol), water (30 mL), and tert-butylhydroperoxide solution (70 wt % in water, 24.5 mL) were combined. The mixture was stirred at room temperature for 1 h, then treated with NaOH (4.7 g, 117.9 mmol), topped with a water condenser and argon inlet, and heated to about 80° C. for about 18 hours. The reaction mixture was then cooled to room temperature, diluted with water, cooled to 0° C., and acidified with HCl to produce reaction mixture D. The reaction mixture D was filtered through filter paper, the solid was discarded, and the filtrate was transferred to a separatory funnel and extracted with ethyl acetate. The combined organic extracts were dried (MgSO$_4$), filtered, and concentrated, then left under vacuum overnight.

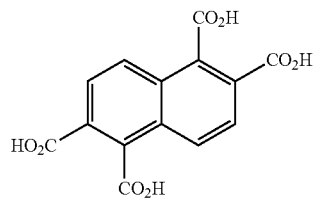 [SMILES: O=C(O)c1ccc2c(C(=O)O)c(C(=O)O)ccc2c1C(=O)O]

was obtained as a brown-orange solid (1.89 g, 6 mmol, 84% yield). The material was carried forward without any purification. The 1H NMR spectrum of

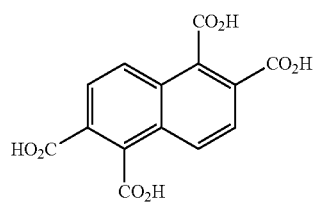 [SMILES: O=C(O)c1ccc2c(C(=O)O)c(C(=O)O)ccc2c1C(=O)O]

is shown in FIG. 5.

The next reaction in the method begins by taking a round bottom flask and combining

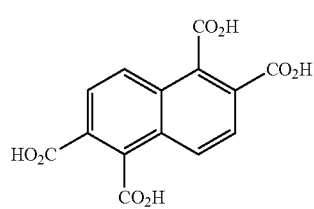 [SMILES: O=C(O)c1ccc2c(C(=O)O)c(C(=O)O)ccc2c1C(=O)O]

(1.89 g, 6.2 mmol) and acetic anhydride (45 mL), then topping with a water condenser and argon inlet, and heating to about 140° C. for about 24 hours to produce reaction mixture E. The reaction mixture E was concentrated, and

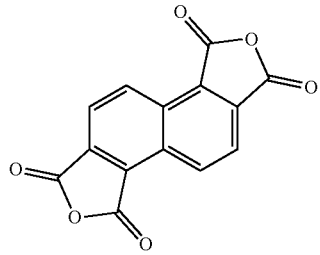

(1.63 g, 6 mmol, 98% yield) was obtained as a dark brown, flaky solid.

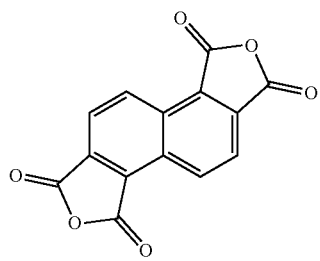

was used without any purification. The 1H NMR spectrum of

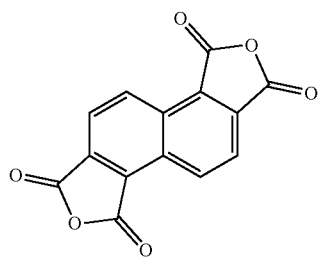 [SMILES: O=c1oc(=O)c2c1ccc1c2ccc2c(=O)oc(=O)c21]

is shown in FIG. 6.

The next step in the method begins by having

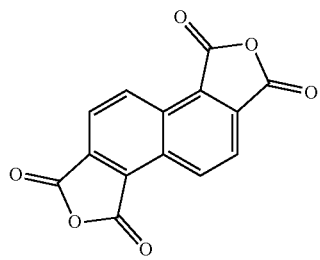 [SMILES: O=c1oc(=O)c2c1ccc1c2ccc2c(=O)oc(=O)c21]

(2.8 g, 10 mmol) in a flask and leaving it under vacuum for about 2 hours. The flask was refilled with argon, and toluene (100 mL) and 2-ethylhexylamine (5.1 mL, 31 mmol) were added. The flask was equipped with a water condenser and argon balloon, and the reaction was heated to about 110° C. for about 18 hours. The reaction mixture was concentrated and the residue was treated with thionyl chloride (60 mL), topped with a water condenser and argon balloon, and heated to about 80° C. for about 5 hours. The thionyl chloride was removed via rotovap, and the remaining residue, reaction mixture F, was dissolved in dichloromethane, adsorbed onto silica gel, and purified on a 100 g Biotage silica gel column with a 30-100% dichloromethane/hexanes gradient. Reaction mixture F was concentrated to produce

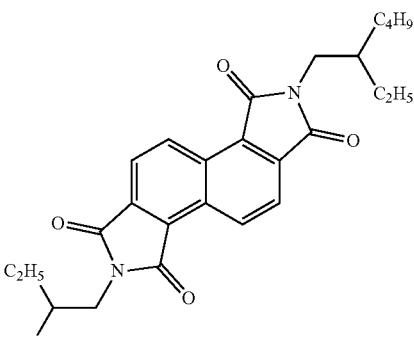

(1.7 g, 3 mmol, 33% yield) as a tan solid. The 1H NMR spectrum of

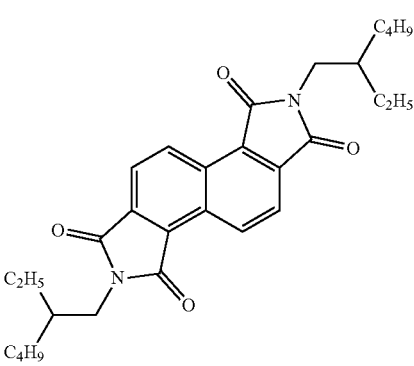

is shown in FIG. 7.

The final step in the method begins by dissolving

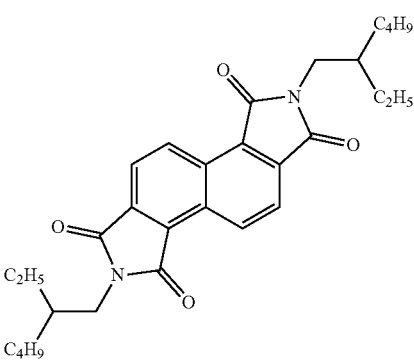

(1.2 g, 2 mmol) in a round bottom flask, with trifluoroacetic acid (12 mL) and sulfuric acid (3 mL), then treated portionwise with N-bromosuccinimide (1.3 g, 7 mmol). The flask was topped with an argon balloon and the reaction was heated to about 55° C. for about 18 hours. Thin layer chromatography of the reaction mixture showed some unreacted starting material, so additional N-bromosuccinimide (0.44 g, 2 mmol) was added, and the reaction stirred at about 55 C for about 1 hour. After cooling to room temperature, the reaction was quenched with ice, then transferred to a separatory funnel and extracted with dichloromethane to produce reaction mixture G. The organic extracts of reaction mixture G was then dried (MgSO$_4$), filtered, and concentrated. The crude material was then dissolved in dichloromethane, adsorbed onto silica, and purified on a 100 g Biotage silica gel column with a 0-100% dichloromethane/hexanes gradient. Reaction mixture G was then concentrated to afford to produce

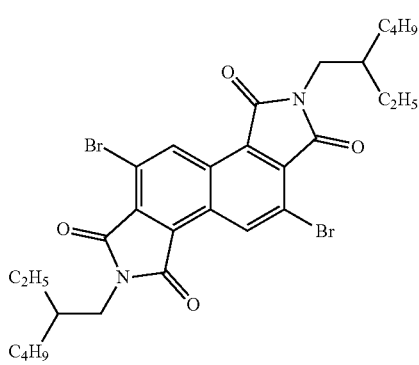

(380 mg, 0.586 mmol, 24% yield) as a yellow solid. The 1H NMR spectrum of

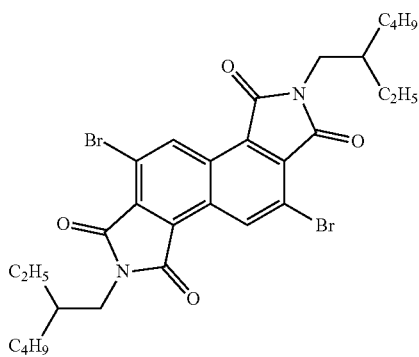

is shown in FIG. 8.

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A method comprising:
converting 2,6-naphthalene diol to produce

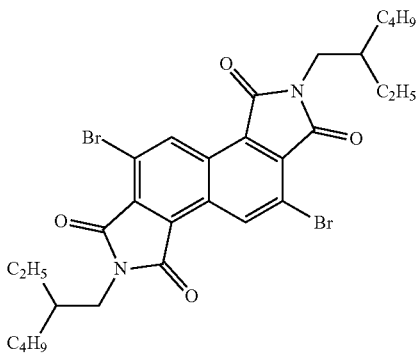

wherein the method occurs at temperatures less than 250° C.

2. The method of claim 1, wherein the conversion does not contain cyanide containing reagents.

3. The method of claim 1, wherein the method comprises a step of brominating 2,6-naphthalene diol to produce

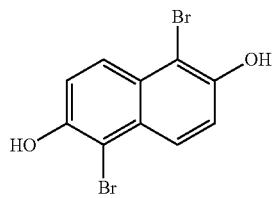 [SMILES: Oc1ccc2c(Br)c(O)ccc2c1Br]

and a step of converting the bromines of

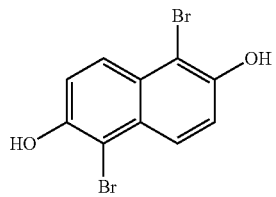 [SMILES: Oc1ccc2c(Br)c(O)ccc2c1Br]

to tetramethylsilane.

4. A method comprising:
a) brominating 2,6-naphthalene diol to produce:

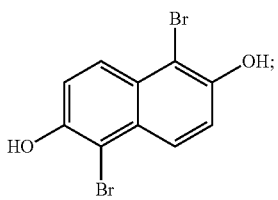

b) converting the diols of

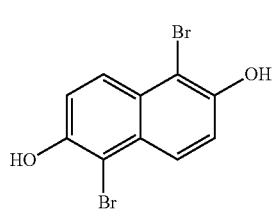 [SMILES: Oc1ccc2c(Br)c(O)ccc2c1Br]

to produce
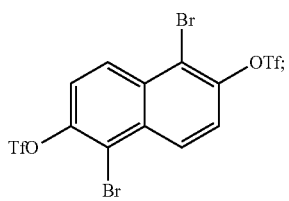 [SMILES: O=S(=O)(Oc1ccc2c(Br)c(OS(=O)(=O)C(F)(F)F)ccc2c1Br)C(F)(F)F]
c) Sonogashira coupling
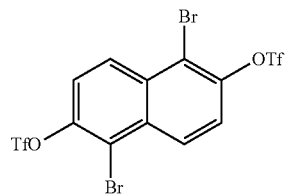 [SMILES: O=S(=O)(Oc1ccc2c(Br)c(OS(=O)(=O)C(F)(F)F)ccc2c1Br)C(F)(F)F]
to produce:
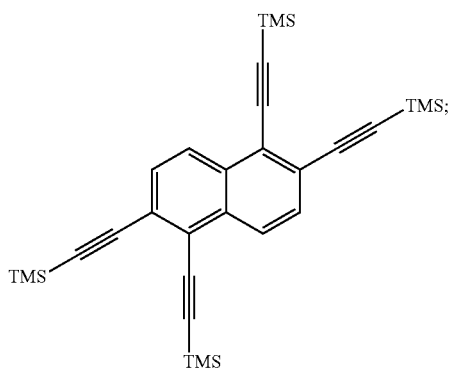 [SMILES: C[Si](C)(C)C#Cc1ccc2c(C#C[Si](C)(C)C)c(C#C[Si](C)(C)C)ccc2c1C#C[Si](C)(C)C]
d) oxidizing
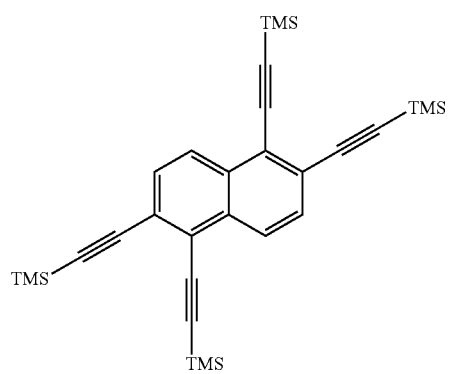 [SMILES: C[Si](C)(C)C#Cc1ccc2c(C#C[Si](C)(C)C)c(C#C[Si](C)(C)C)ccc2c1C#C[Si](C)(C)C]
to produce:
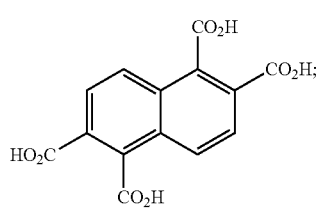 [SMILES: O=C(O)c1ccc2c(C(=O)O)c(C(=O)O)ccc2c1C(=O)O]
e) cyclizing
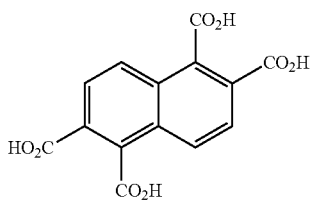 [SMILES: O=C(O)c1ccc2c(C(=O)O)c(C(=O)O)ccc2c1C(=O)O]
to produce:
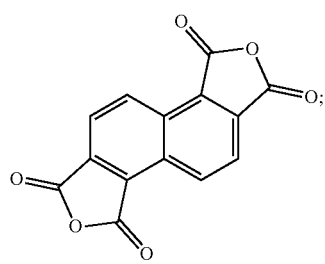 [SMILES: O=c1oc(=O)c2c1ccc1c2ccc2c(=O)oc(=O)c21]
f) converting
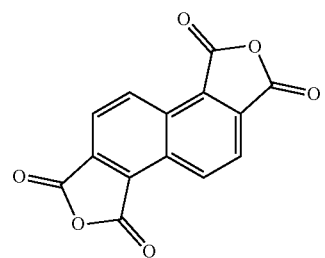 [SMILES: O=c1oc(=O)c2c1ccc1c2ccc2c(=O)oc(=O)c21]
to produce:
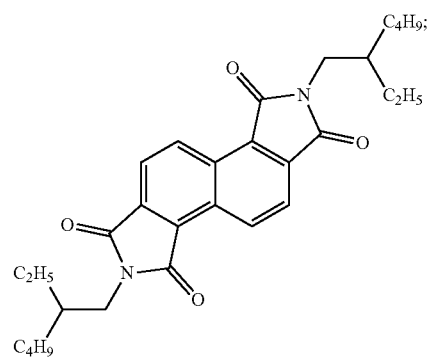
g) brominating
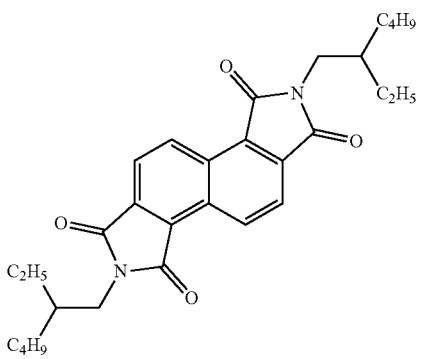

to produce:

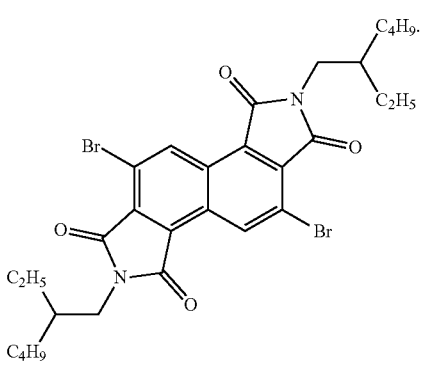

5. The method of claim 4, wherein the method occurs at temperatures less than 250° C.

6. The method of claim 4, wherein the conversion does not contain cyanide containing reagents.

7. A method comprising:

a) reacting 2,6-naphthalene diol to produce reaction mixture A, wherein reaction mixture A comprises:

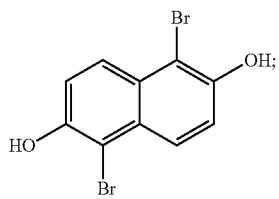 [SMILES: Oc1ccc2c(Br)c(O)ccc2c1Br]

b) reacting

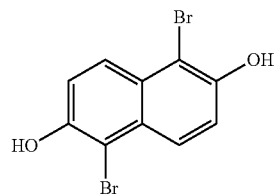

to produce reaction mixture B, wherein reaction mixture B comprises:

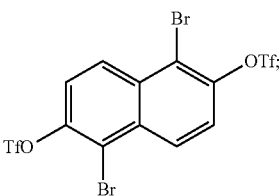 [SMILES: O=S(=O)(Oc1ccc2c(Br)c(OS(=O)(=O)C(F)(F)F)ccc2c1Br)C(F)(F)F]

c) reacting

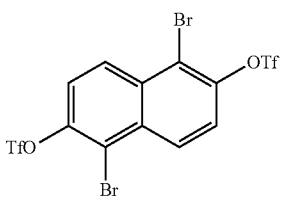 [SMILES: O=S(=O)(Oc1ccc2c(Br)c(OS(=O)(=O)C(F)(F)F)ccc2c1Br)C(F)(F)F]

to produce reaction mixture C, wherein reaction mixture C comprises:

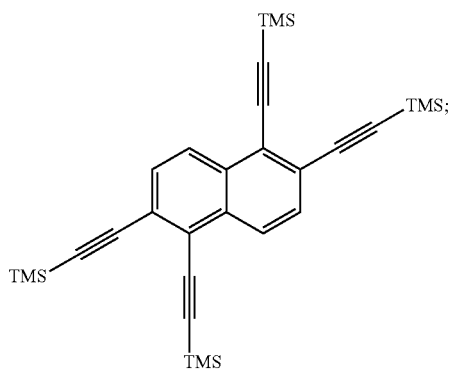 [SMILES: C[Si](C)(C)C#Cc1ccc2c(C#C[Si](C)(C)C)c(C#C[Si](C)(C)C)ccc2c1C#C[Si](C)(C)C]

d) reacting

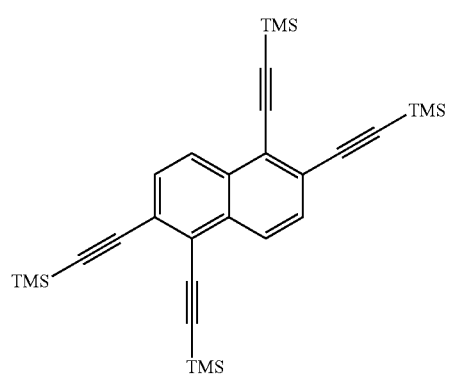 [SMILES: C[Si](C)(C)C#Cc1ccc2c(C#C[Si](C)(C)C)c(C#C[Si](C)(C)C)ccc2c1C#C[Si](C)(C)C]

to produce reaction mixture D, wherein reaction mixture D comprises:

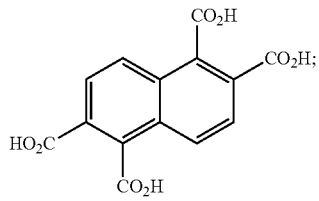 [SMILES: O=C(O)c1ccc2c(C(=O)O)c(C(=O)O)ccc2c1C(=O)O]

e) reacting

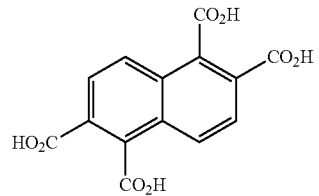 [SMILES: O=C(O)c1ccc2c(C(=O)O)c(C(=O)O)ccc2c1C(=O)O]

to produce reaction mixture E, wherein reaction mixture E comprises:

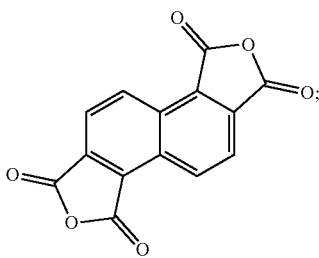 [SMILES: O=c1oc(=O)c2c1ccc1c2ccc2c(=O)oc(=O)c21]

f) reacting

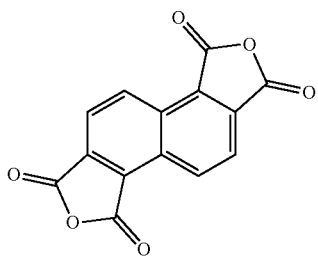 [SMILES: O=c1oc(=O)c2c1ccc1c2ccc2c(=O)oc(=O)c21]

to produce reaction mixture F, wherein reaction mixture F comprises:

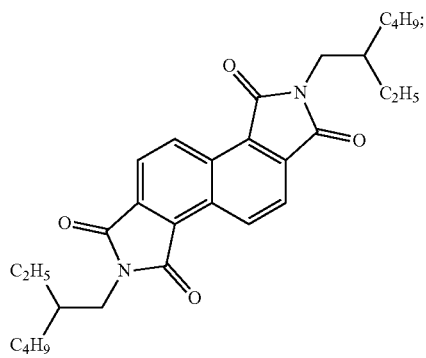

g) reacting

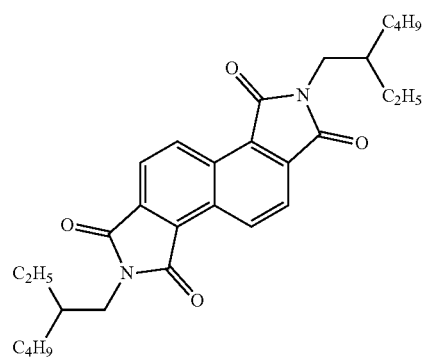

to produce reaction mixture G, wherein reaction mixture G comprises:

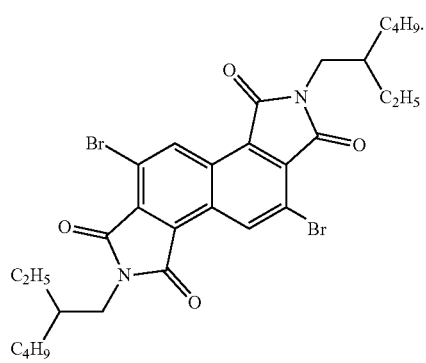

8. The method of claim 7, wherein the method occurs at temperatures less than 250° C.

9. The method of claim 7, wherein the conversion does not contain cyanide.

10. A method comprising:

a) reacting 2,6-naphthalene diol in tetrahydofuran with N-bromosuccinimide, at a temperature below about 20° C., to produce reaction mixture A, reaction mixture A is then diluted with $Na_2S_2O_3$, at a temperature greater than about 20° C. and less than 250° C., and filtered to produce

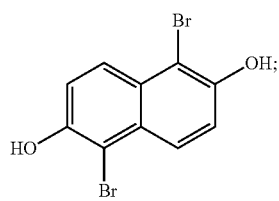

b) reacting

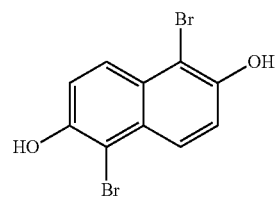 [SMILES: Oc1ccc2c(Br)c(O)ccc2c1Br]

with triflic anhydride, at a temperature below about 20° C., followed by pyridine, at a temperature below about 20° C., to produce reaction mixture B, reaction mixture B is then diluted with dichloromethane and fractionated to produce

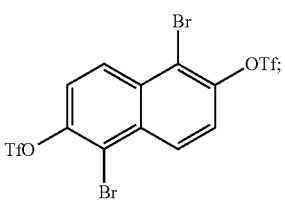 [SMILES: O=S(=O)(Oc1ccc2c(Br)c(OS(=O)(=O)C(F)(F)F)ccc2c1Br)C(F)(F)F]

c) reacting

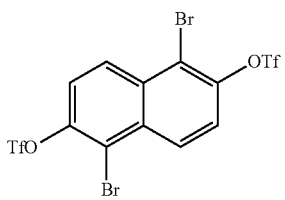 [SMILES: O=S(=O)(Oc1ccc2c(Br)c(OS(=O)(=O)C(F)(F)F)ccc2c1Br)C(F)(F)F]

with CuI and $Pd(PPh_3)_2Cl_2$, followed by trimethylamine and trimethylsilylacetylene to produce reaction mixture C, reaction mixture C is then extracted with dicholoromethane and fractionated to produce

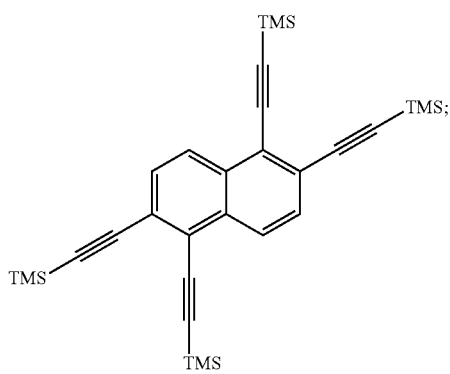 [SMILES: C[Si](C)(C)C#Cc1ccc2c(C#C[Si](C)(C)C)c(C#C[Si](C)(C)C)ccc2c1C#C[Si](C)(C)C]

d) reacting

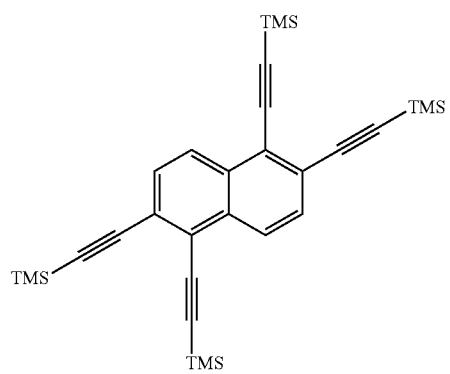 [SMILES: C[Si](C)(C)C#Cc1ccc2c(C#C[Si](C)(C)C)c(C#C[Si](C)(C)C)ccc2c1C#C[Si](C)(C)C]

with FeCl$_3$ and a tert-butylhydroperoxide solution followed by a NaOH treatment and acidification with HCl to produce reaction mixture D, reaction mixture D is then filtered and dried to produce

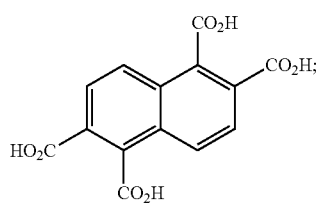 [SMILES: O=C(O)c1ccc2c(C(=O)O)c(C(=O)O)ccc2c1C(=O)O]

e) reacting

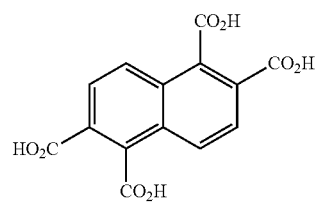

with acetic anhydride, at temperature greater than about 20° C. and less than 250° C., to produce reaction mixture E which comprises:

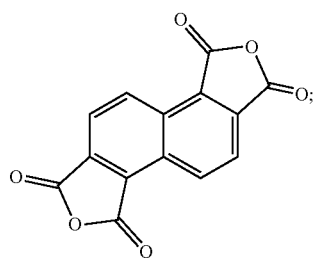 [SMILES: O=c1oc(=O)c2c1ccc1c2ccc2c(=O)oc(=O)c21]

f) reacting

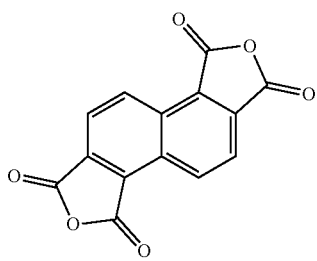 [SMILES: O=c1oc(=O)c2c1ccc1c2ccc2c(=O)oc(=O)c21]

with 2-ethylhexylamine and toluene, at temperature greater than about 20° C. and less than 250° C., followed by reacting with thionyl chloride to produce reaction mixture F, reaction mixture F is then purified to produce

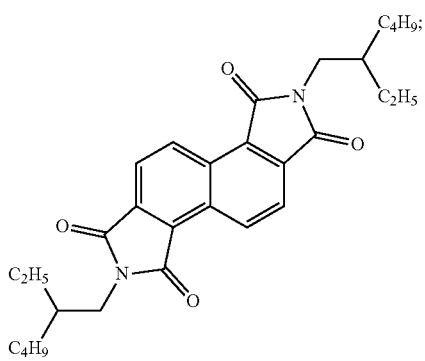

g) reacting

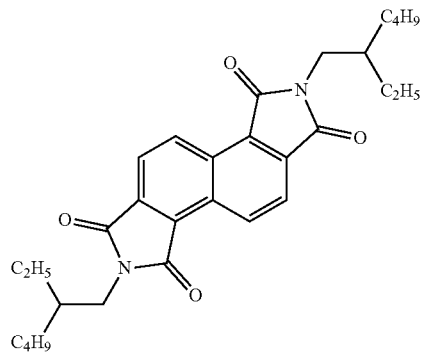

with N-bromosuccinimide, at temperature greater than about 20° C. and less than 250° C., to produce reaction mixture G, reaction mixture G is then purified to produce

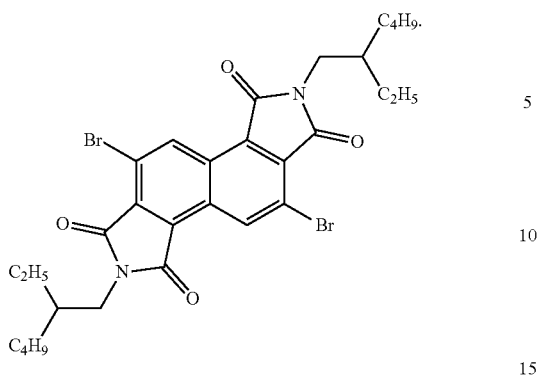
11. The method of claim 10, wherein the method occurs at temperatures less than 250° C.
12. The method of claim 10, wherein the conversion does not contain cyanide containing reagents.
* * * * *